United States Patent
Makin et al.

(10) Patent No.: US 7,494,467 B2
(45) Date of Patent: Feb. 24, 2009

(54) MEDICAL SYSTEM HAVING MULTIPLE ULTRASOUND TRANSDUCERS OR AN ULTRASOUND TRANSDUCER AND AN RF ELECTRODE

(75) Inventors: Inder Raj S. Makin, Loveland, OH (US); T. Douglas Mast, Cincinnati, OH (US); Michael H. Slayton, Tempe, AZ (US); Peter G. Barthe, Phoenix, AZ (US); Jeffrey D. Messerly, Cincinnati, OH (US); Waseem Faidi, Clifton Park, NY (US); Megan M. Runk, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 773 days.

(21) Appl. No.: 10/825,952

(22) Filed: Apr. 16, 2004

(65) Prior Publication Data

US 2005/0240125 A1 Oct. 27, 2005

(51) Int. Cl.
*A61B 8/00* (2006.01)
*A61H 1/00* (2006.01)

(52) U.S. Cl. .................. 600/439; 600/437; 600/459; 600/462; 601/2

(58) Field of Classification Search .......... 600/439, 600/437, 459, 462; 607/97; 601/2
See application file for complete search history.

(56) References Cited

U.S. PATENT DOCUMENTS

| 3,168,659 | A | 2/1965 | Bayre et al. |
|---|---|---|---|
| 3,902,501 | A | 9/1975 | Citron et al. |
| 3,927,557 | A | 12/1975 | Viertl |
| 4,315,514 | A | 2/1982 | Drewes et al. |
| 4,323,077 | A | 4/1982 | Smith |
| 4,484,569 | A | 11/1984 | Driller et al. |
| 4,646,756 | A | 3/1987 | Watmough et al. |
| 4,748,985 | A | 6/1988 | Nagasaki |
| 4,757,820 | A | 7/1988 | Itoh |
| 4,787,394 | A | 11/1988 | Ogura |
| 4,798,215 | A | 1/1989 | Turner |

(Continued)

FOREIGN PATENT DOCUMENTS

JP 10-14967 1/1998

(Continued)

OTHER PUBLICATIONS

Hill, C.R. et al., Lesion Development In Focused Ultrasound Surgery: A General Model, Ultrasound in Med. & Biol., 1994, pp. 259-269, vol. 20, No. 3, Elsevier Science Ltd, New York, USA.

(Continued)

*Primary Examiner*—Eric F Winakur
*Assistant Examiner*—Katherine L Fernandez
(74) *Attorney, Agent, or Firm*—Verne E. Kreger, Jr.

(57) ABSTRACT

An ultrasound medical system includes an ultrasound transducer assembly having various combinations of ultrasound transducers having different-shaped ultrasound emitting surfaces and/or different ultrasound transducer types, wherein the types are ultrasound-medical-treatment-only type, ultrasound-medical-treatment-and-imaging type, and ultrasound-medical-imaging-only type ultrasound transducers. Another ultrasound medical system includes a transducer assembly having an RF (radio-frequency) medical-treatment electrode and an ultrasound medical transducer.

22 Claims, 4 Drawing Sheets

U.S. PATENT DOCUMENTS

| | | |
|---|---|---|
| 4,818,954 A | 4/1989 | Flachenecker et al. |
| 4,844,080 A | 7/1989 | Frass et al. |
| 4,858,613 A | 8/1989 | Fry et al. |
| 4,932,414 A | 6/1990 | Coleman et al. |
| 4,937,767 A | 6/1990 | Reuschel et al. |
| 4,951,653 A | 8/1990 | Fry et al. |
| 4,955,365 A | 9/1990 | Fry et al. |
| 4,955,366 A | 9/1990 | Uchiyama et al. |
| 4,960,107 A | 10/1990 | Aida et al. |
| 4,960,109 A | 10/1990 | Lele |
| 4,984,575 A | 1/1991 | Uchiyama et al. |
| 4,986,275 A | 1/1991 | Ishida et al. |
| RE33,590 E | 5/1991 | Dory |
| 5,015,929 A | 5/1991 | Cathignol et al. |
| 5,036,855 A | 8/1991 | Fry et al. |
| 5,054,470 A | 10/1991 | Fry et al. |
| 5,065,740 A | 11/1991 | Itoh |
| 5,078,144 A | 1/1992 | Sekino et al. |
| 5,080,101 A | 1/1992 | Dory |
| 5,080,102 A | 1/1992 | Dory |
| 5,095,907 A | 3/1992 | Kudo et al. |
| 5,117,832 A | 6/1992 | Sanghvi et al. |
| 5,143,073 A | 9/1992 | Dory |
| 5,143,074 A | 9/1992 | Dory |
| 5,149,319 A | 9/1992 | Unger |
| 5,150,711 A | 9/1992 | Dory |
| 5,150,712 A | 9/1992 | Dory |
| 5,158,070 A | 10/1992 | Dory |
| 5,158,071 A | 10/1992 | Umemura et al. |
| 5,203,333 A | 4/1993 | Nomura |
| 5,209,221 A | 5/1993 | Riedlinger |
| 5,238,007 A | 8/1993 | Giele et al. |
| 5,240,005 A | 8/1993 | Viebach |
| 5,242,437 A | 9/1993 | Everett et al. |
| 5,295,484 A | 3/1994 | Marcus et al. |
| 5,304,115 A | 4/1994 | Pflueger et al. |
| 5,305,731 A | 4/1994 | Buchholtz |
| 5,311,869 A | 5/1994 | Okazaki |
| 5,348,017 A | 9/1994 | Thornton et al. |
| 5,354,258 A | 10/1994 | Dory |
| 5,391,140 A | 2/1995 | Schaetzle et al. |
| 5,391,197 A | 2/1995 | Burdette et al. |
| 5,402,792 A | 4/1995 | Kimura |
| 5,409,002 A | 4/1995 | Pell |
| 5,413,550 A | 5/1995 | Castel |
| 5,419,335 A | 5/1995 | Hartmann et al. |
| 5,431,663 A | 7/1995 | Carter |
| 5,435,304 A | 7/1995 | Oppelt et al. |
| 5,435,311 A | 7/1995 | Umemura et al. |
| 5,443,069 A | 8/1995 | Schaetzle |
| 5,448,994 A | 9/1995 | Iinuma |
| 5,458,597 A | 10/1995 | Edwards et al. |
| 5,465,724 A | 11/1995 | Sliwa et al. |
| 5,471,988 A * | 12/1995 | Fujio et al. ................. 600/439 |
| 5,474,071 A | 12/1995 | Chapelon et al. |
| 5,485,839 A | 1/1996 | Aida et al. |
| 5,492,126 A | 2/1996 | Hennige et al. |
| 5,500,012 A | 3/1996 | Brucker et al. |
| 5,501,655 A | 3/1996 | Rolt et al. |
| 5,514,085 A | 5/1996 | Yoon |
| 5,514,130 E | 5/1996 | Baker |
| 5,520,188 A | 5/1996 | Hennige et al. |
| 5,522,869 A | 6/1996 | Burdette et al. |
| 5,524,620 A | 6/1996 | Rosenschein |
| 5,526,815 A | 6/1996 | Granz et al. |
| 5,526,822 A | 6/1996 | Burbank et al. |
| 5,540,656 A | 7/1996 | Pflueger et al. |
| 5,545,195 A | 8/1996 | Lennox et al. |
| 5,547,459 A | 8/1996 | Kaufman et al. |
| 5,549,638 A | 8/1996 | Burdette |
| 5,558,092 A * | 9/1996 | Unger et al. ................. 600/439 |
| 5,569,241 A | 10/1996 | Edwards |
| 5,571,088 A | 11/1996 | Lennox et al. |
| 5,573,497 A | 11/1996 | Chapelon |
| 5,575,288 A | 11/1996 | Sliwa et al. |
| 5,575,772 A | 11/1996 | Lennox |
| 5,575,789 A | 11/1996 | Bell et al. |
| 5,582,588 A | 12/1996 | Sakurai et al. |
| 5,588,432 A | 12/1996 | Crowley |
| 5,590,657 A | 1/1997 | Cain et al. |
| 5,601,526 A | 2/1997 | Chapelon et al. |
| 5,620,479 A * | 4/1997 | Diederich ...................... 601/3 |
| 5,624,382 A | 4/1997 | Oppelt et al. |
| 5,628,743 A | 5/1997 | Cimino |
| 5,630,837 A | 5/1997 | Crowley |
| 5,643,179 A | 7/1997 | Fujimoto |
| 5,649,547 A | 7/1997 | Ritchart et al. |
| 5,657,760 A | 8/1997 | Ying et al. |
| 5,665,054 A | 9/1997 | Dory |
| 5,666,954 A | 9/1997 | Chapelon et al. |
| 5,676,692 A | 10/1997 | Sanghvi et al. |
| 5,687,729 A | 11/1997 | Schaetzle |
| 5,694,936 A | 12/1997 | Fujimoto et al. |
| 5,697,897 A | 12/1997 | Buchholtz et al. |
| 5,699,804 A | 12/1997 | Rattner |
| 5,703,922 A | 12/1997 | Rattner |
| 5,715,825 A | 2/1998 | Crowley |
| 5,720,287 A | 2/1998 | Chapelon et al. |
| 5,722,411 A | 3/1998 | Suzuki et al. |
| 5,728,062 A | 3/1998 | Brisken |
| 5,733,315 A | 3/1998 | Burdette et al. |
| 5,735,280 A | 4/1998 | Sherman et al. |
| 5,735,796 A | 4/1998 | Granz et al. |
| 5,738,635 A | 4/1998 | Chapelon et al. |
| 5,743,862 A | 4/1998 | Izumi |
| 5,743,863 A | 4/1998 | Chapelon |
| 5,746,224 A | 5/1998 | Edwards |
| 5,759,154 A | 6/1998 | Hoyns |
| 5,759,162 A | 6/1998 | Oppelt et al. |
| 5,762,066 A | 6/1998 | Law et al. |
| 5,769,086 A | 6/1998 | Ritchart et al. |
| 5,769,790 A | 6/1998 | Watkins et al. |
| 5,771,896 A | 6/1998 | Sliwa et al. |
| 5,785,705 A | 7/1998 | Baker |
| 5,788,636 A | 8/1998 | Curley |
| 5,800,379 A | 9/1998 | Edwards |
| 5,807,308 A | 9/1998 | Edwards |
| 5,817,021 A | 10/1998 | Reichenberger |
| 5,817,049 A | 10/1998 | Edwards |
| 5,820,580 A | 10/1998 | Edwards et al. |
| 5,823,962 A | 10/1998 | Schaetzle et al. |
| 5,836,896 A | 11/1998 | Rosenschein |
| 5,840,031 A | 11/1998 | Crowley |
| 5,860,974 A | 1/1999 | Abele |
| 5,873,828 A | 2/1999 | Fujio et al. |
| 5,873,845 A | 2/1999 | Cline et al. |
| 5,873,902 A | 2/1999 | Sanghvi et al. |
| 5,876,399 A | 3/1999 | Chia et al. |
| 5,882,302 A | 3/1999 | Driscoll, Jr. et al. |
| 5,895,356 A | 4/1999 | Andrus et al. |
| 5,897,495 A | 4/1999 | Aida et al. |
| 5,897,523 A | 4/1999 | Wright et al. |
| 5,928,169 A | 7/1999 | Schatzle et al. |
| 5,931,848 A | 8/1999 | Saadat |
| 5,938,600 A | 8/1999 | Van Vaals et al. |
| 5,938,608 A | 8/1999 | Bieger et al. |
| 5,944,663 A | 8/1999 | Kuth et al. |
| 5,964,755 A | 10/1999 | Edwards |
| 5,979,453 A | 11/1999 | Savage et al. |
| 5,984,881 A | 11/1999 | Ishibashi et al. |
| 5,984,882 A | 11/1999 | Rosenschein et al. |
| 5,993,389 A | 11/1999 | Driscoll, Jr. et al. |
| 5,997,534 A | 12/1999 | Tu et al. |
| 6,001,069 A | 12/1999 | Tachibana et al. |

| | | | | | |
|---|---|---|---|---|---|
| 6,004,269 A | 12/1999 | Crowley et al. | 2002/0087081 A1 | 7/2002 | Serrano et al. |
| 6,007,499 A | 12/1999 | Martin et al. | 2002/0087083 A1 | 7/2002 | Nix et al. |
| 6,022,319 A | 2/2000 | Willard et al. | 2002/0111662 A1 | 8/2002 | Iaizzo et al. |
| 6,024,718 A | 2/2000 | Chen et al. | 2002/0165579 A1 | 11/2002 | Burbank et al. |
| 6,024,740 A | 2/2000 | Lesh et al. | 2002/0183742 A1 | 12/2002 | Carmel et al. |
| 6,039,689 A | 3/2000 | Lizzi | 2002/0183771 A1 | 12/2002 | Burbank et al. |
| 6,042,556 A | 3/2000 | Beach et al. | 2002/0193781 A1 | 12/2002 | Loeb |
| 6,050,943 A | 4/2000 | Slayton et al. | 2003/0004434 A1 | 1/2003 | Greco et al. |
| 6,066,123 A | 5/2000 | Li et al. | 2003/0013960 A1 | 1/2003 | Makin et al. |
| 6,071,238 A | 6/2000 | Chapelon et al. | 2003/0013971 A1 | 1/2003 | Makin et al. |
| 6,071,239 A | 6/2000 | Cribbs et al. | 2003/0018266 A1 * | 1/2003 | Makin et al. ............. 600/459 |
| 6,083,159 A | 7/2000 | Driscoll, Jr. et al. | 2003/0018358 A1 | 1/2003 | Saadat |
| 6,086,535 A | 7/2000 | Ishibashi et al. | 2003/0028111 A1 | 2/2003 | Vaezy et al. |
| 6,088,613 A | 7/2000 | Unger | 2003/0040698 A1 | 2/2003 | Makin et al. |
| 6,106,469 A | 8/2000 | Suzuki et al. | 2003/0047582 A1 | 3/2003 | Sonnenschein et al. |
| 6,106,517 A | 8/2000 | Zupkas | 2003/0073907 A1 | 4/2003 | Taylor |
| 6,112,123 A | 8/2000 | Kelleher et al. | 2003/0109786 A1 | 6/2003 | Irioka et al. |
| 6,113,558 A | 9/2000 | Rosenschein et al. | 2003/0120270 A1 | 6/2003 | Acker |
| 6,117,101 A | 9/2000 | Diederich et al. | 2003/0144593 A1 | 7/2003 | Whitmore et al. |
| 6,135,963 A | 10/2000 | Haider | 2003/0212331 A1 | 11/2003 | Fenton et al. |
| 6,135,971 A | 10/2000 | Hutchinson et al. | 2003/0212332 A1 | 11/2003 | Fenton et al. |
| 6,138,513 A | 10/2000 | Barabash et al. | 2003/0220568 A1 | 11/2003 | Hansmann et al. |
| 6,171,248 B1 * | 1/2001 | Hossack et al. ............. 600/459 | 2004/0006336 A1 | 1/2004 | Swanson |
| 6,176,842 B1 | 1/2001 | Tachibana et al. | 2004/0030268 A1 | 2/2004 | Weng et al. |
| 6,183,469 B1 | 2/2001 | Thapliyal et al. | 2004/0143252 A1 | 7/2004 | Hurst |
| 6,210,330 B1 | 4/2001 | Tepper | 2004/0254570 A1 | 12/2004 | Hadjicostis et al. |
| 6,216,704 B1 | 4/2001 | Ingle et al. | 2005/0015107 A1 | 1/2005 | O'Brien |
| 6,217,576 B1 | 4/2001 | Tu et al. | 2005/0085726 A1 | 4/2005 | Lacoste et al. |
| 6,231,834 B1 | 5/2001 | Unger et al. | 2005/0137520 A1 | 6/2005 | Rule et al. |
| 6,352,532 B1 | 3/2002 | Kramer et al. | 2005/0228286 A1 | 10/2005 | Messerly et al. |
| 6,361,531 B1 | 3/2002 | Hissong | 2005/0261585 A1 | 11/2005 | Makin et al. |
| 6,371,903 B1 | 4/2002 | Blanc et al. | 2005/0261587 A1 | 11/2005 | Makin et al. |
| 6,379,320 B1 | 4/2002 | Lafon et al. | 2005/0261588 A1 | 11/2005 | Makin et al. |
| 6,425,867 B1 | 7/2002 | Vaezy et al. | 2005/0267488 A1 | 12/2005 | Hare et al. |
| 6,482,178 B1 | 11/2002 | Andrews et al. | 2006/0052701 A1 | 3/2006 | Carter et al. |
| 6,508,774 B1 | 1/2003 | Acker et al. | 2006/0173348 A1 | 8/2006 | Wilser et al. |
| 6,512,957 B1 | 1/2003 | Witte | 2006/0235306 A1 | 10/2006 | Cotter et al. |
| 6,521,211 B1 | 2/2003 | Unger et al. | 2007/0021691 A1 | 1/2007 | Nita et al. |
| 6,533,726 B1 | 3/2003 | Lizzi et al. | | | |
| 6,546,934 B1 | 4/2003 | Ingle et al. | | | |
| 6,575,956 B1 | 6/2003 | Brisken et al. | | | |
| 6,599,245 B1 | 7/2003 | Ma et al. | | | |
| 6,602,251 B2 | 8/2003 | Burbank et al. | | | |
| 6,613,004 B1 * | 9/2003 | Vitek et al. ..................... 601/2 | | | |
| 6,618,620 B1 | 9/2003 | Freundlich et al. | | | |
| 6,626,855 B1 | 9/2003 | Weng et al. | | | |
| 6,645,202 B1 | 11/2003 | Pless et al. | | | |
| 6,669,638 B1 | 12/2003 | Miller et al. | | | |
| 6,716,184 B2 * | 4/2004 | Vaezy et al. ................... 601/3 | | | |
| 6,719,694 B2 | 4/2004 | Weng et al. | | | |
| 6,764,488 B1 | 7/2004 | Burbank et al. | | | |
| 6,770,070 B1 * | 8/2004 | Balbierz ..................... 606/41 | | | |
| 6,887,239 B2 | 5/2005 | Elstrom et al. | | | |
| 6,902,536 B2 * | 6/2005 | Manna et al. .................. 601/2 | | | |
| 6,921,371 B2 | 7/2005 | Wilson | | | |
| 6,936,024 B1 | 8/2005 | Houser | | | |
| 6,936,048 B2 | 8/2005 | Hurst | | | |
| 6,974,417 B2 | 12/2005 | Lockwood et al. | | | |
| 7,037,306 B2 | 5/2006 | Podany et al. | | | |
| 7,063,666 B2 * | 6/2006 | Weng et al. .................. 600/439 | | | |
| 7,078,015 B2 | 7/2006 | Unger | | | |
| 2001/0007940 A1 | 7/2001 | Tu et al. | | | |
| 2001/0014805 A1 | 8/2001 | Burbank et al. | | | |
| 2001/0037073 A1 | 11/2001 | White et al. | | | |
| 2002/0065512 A1 | 5/2002 | Fjeld et al. | | | |
| 2002/0068934 A1 | 6/2002 | Edwards et al. | | | |

FOREIGN PATENT DOCUMENTS

WO     WO 01/45550 A2     6/2001

OTHER PUBLICATIONS

Clare, M.C. et al., MRI Guided Focused Ultrasound Surgery (FUS) of uterine leiomyomas: A Feasibility Study, Workshop on MRI-Guided: Focused Ultrasound Surgery, 2002, Syllabus, International Society for Magnetic Resonance in Medicine.

Vaezy, S. et al., Treatment Of Uterine Fibroid Tumors In A Nude Mouse Model Using High-Intensity Focused Ultrasound, Am J Obstet Gynecol, 2000, pp. 6-11, vol. 183, No. 1.

Cool-tip™ RF Tadio Frequency Ablation System, web page from radionics.com.

Electrosurgical Devices, RF Generator and RITA Base Software, web pages from ritamedical.com.

Chavrier et al., "Modeling of high-intensity focused ultrasound-induced lesions in the presence of cavitation bubbles," J. Acoust. Soc. Am. 108 (1), pp. 432-440 (Jul. 2000).

Watkins et al., "High-intensity focused ultrasound ablation of the kidney in a large animal model," J. Endourol., 11 (3), 191, abstract (Jun. 1997).

Billard, et al., "Effects of Physical Parameters in High Temperature Ultrasound Hyperthermia," *Ultrasound in Medicine and Biology*, vol. 16, Issue 4, pp. 409-420 (1990).

* cited by examiner

MEDICAL SYSTEM HAVING MULTIPLE ULTRASOUND TRANSDUCERS OR AN ULTRASOUND TRANSDUCER AND AN RF ELECTRODE

FIELD OF THE INVENTION

The present invention relates generally to ultrasound, and more particularly to an ultrasound medical system having a transducer assembly including multiple ultrasound transducers or an ultrasound transducer and an RF (radio-frequency) electrode.

BACKGROUND OF THE INVENTION

Known ultrasound medical systems include medical systems which use ultrasound imaging of patients to identify patient tissue for medical treatment and which use ultrasound to ablate identified patient tissue (i.e., medically destroy patient tissue by heating the tissue to form a lesion). In one known design, an ultrasound-medical-imaging-only ultrasound transducer is attached on one side of a rotatable shaft and an ultrasound-medical-treatment-only ultrasound transducer is attached on the opposite side of the shaft. In another known design, the ultrasound transducer is an ultrasound-medical-treatment-and-imaging ultrasound transducer wherein medical imaging is done at a lower power and medical treatment is done at a higher power.

In one known example, a transducer assembly includes a single ultrasound transducer having a single transducer element, or an array of transducer elements acting together, to ultrasonically image the patient and/or to ultrasonically ablate identified patient tissue. A known transducer element includes a transducer element having a concave shape to focus ultrasound energy. A known array of transducer elements includes a planar, concave, or convex array of transducer elements. A known array of transducer elements includes an array whose transducer elements are electronically or mechanically controlled together to steer and focus the ultrasound emitted by the array to a focal zone (which may be large or which may be as small as, for example, a grain of rice) to provide three-dimensional medical ultrasound treatment of patient tissue.

Known ultrasound medical systems include medical systems which: deploy an end effector having an ultrasound transducer outside the body to break up kidney stones inside the body; endoscopically insert an end effector having an ultrasound transducer in the rectum to medically destroy prostate cancer; laparoscopically insert an end effector having an ultrasound transducer in the abdominal cavity to medically destroy a cancerous liver tumor; intravenously insert a catheter end effector having an ultrasound transducer into a vein in the arm and moves the catheter to the heart to medically destroy diseased heart tissue; and interstitially insert a needle end effector having an ultrasound transducer needle into the tongue to medically destroy tissue to reduce tongue volume to reduce snoring.

Still, scientists and engineers continue to seek improved ultrasound medical systems.

SUMMARY OF THE INVENTION

A first embodiment of the invention is an ultrasound medical system including an ultrasound transducer assembly which has a longitudinal axis and a distal end. The ultrasound transducer assembly includes first, second and third ultrasound transducers. The first ultrasound transducer is located proximate the distal end and has a substantially-fully-cylindrical ultrasound-emitting surface which is substantially coaxially aligned with, and outwardly-facing from, the longitudinal axis. The second ultrasound transducer has a substantially-fully-cylindrical ultrasound-emitting surface which is substantially coaxially aligned with, and outwardly-facing from, the longitudinal axis. The third ultrasound transducer is positioned longitudinally between the first and second ultrasound transducers and has an ultrasound-emitting surface which is substantially-entirely planar or includes at least a concave surface portion.

A broadened expression of the first embodiment is for an ultrasound medical system including an ultrasound transducer assembly having a longitudinal axis, having a distal end, and having two ultrasound transducers. One of the ultrasound transducers has a substantially-fully-cylindrical ultrasound-emitting surface which is substantially coaxially aligned with, and outwardly-facing from, the longitudinal axis. An other of the ultrasound transducers is positioned longitudinally proximal or distal to the one ultrasound transducer and has an ultrasound-emitting surface which is substantially-entirely planar or includes at least a concave surface portion.

A second embodiment of the invention is an ultrasound medical system including an ultrasound transducer assembly having a longitudinal axis. The ultrasound transducer assembly includes first, second and third ultrasound transducers each having an ultrasound-emitting surface which is substantially-entirely planar or includes at least a concave surface portion. The first and second ultrasound transducers are ultrasound-medical-treatment-only ultrasound transducers. The third ultrasound transducer is an ultrasound-medical-treatment-and-imaging ultrasound transducer positioned longitudinally between the first and second ultrasound transducers.

A third embodiment of the invention is an ultrasound medical system including an ultrasound transducer assembly having a longitudinal axis. The ultrasound transducer assembly includes first, second and third ultrasound transducers each having an ultrasound-emitting surface which is substantially-entirely planar or includes at least a concave surface portion. The first and second ultrasound transducers are ultrasound-medical-treatment-only ultrasound transducers. The third ultrasound transducer is an ultrasound-medical-imaging-only ultrasound transducer positioned longitudinally between the first and second ultrasound transducers.

A fourth embodiment of the invention is an ultrasound medical system including an ultrasound transducer assembly having a longitudinal axis. The ultrasound transducer assembly includes first, second and third ultrasound transducers each having an ultrasound-emitting surface which is substantially-entirely planar or includes at least a concave surface portion. The first and second ultrasound transducers are ultrasound-medical-treatment-and-imaging ultrasound transducers. The third ultrasound transducer is an ultrasound-medical-treatment-only ultrasound transducer positioned longitudinally between the first and second ultrasound transducers.

A broadened expression of the second through fourth embodiments is for an ultrasound medical system including an ultrasound transducer assembly having a longitudinal axis, and having two ultrasound transducers each having an ultrasound-emitting surface which is substantially-entirely planar or includes at least a concave surface portion. One of the ultrasound transducers is positioned longitudinally proximal or distal to an other of the ultrasound transducers. The one and the other ultrasound transducers are different types of medical-treatment-only type, medical-treatment-and-imaging type, and medical-imaging-only type transducers.

A fifth embodiment of the invention is an ultrasound medical system including a transducer assembly having a longitudinal axis, having a distal end, having a first RF (radio-frequency) medical-treatment electrode, and having an ultrasound medical transducer positioned longitudinally proximal or distal to the first RF medical-treatment electrode.

Several benefits and advantages are obtained from one or more of the embodiments of the ultrasound medical system of the invention. In one example of the first embodiment, the first and second ultrasound transducers are ultrasound-medical-treatment-only ultrasound transducers and the third ultrasound transducer is an ultrasound-medical-treatment-and-imaging ultrasound transducer which provides 360-degree treatment of patient tissue from the first and second transducers while also providing imaging (and treatment) from the third transducer. The second, third and fourth embodiments provide, in one example, treatment (from treat-only or treat-and-image first and second transducers) at the longitudinal ends of the transducer assembly which enhances the axial (longitudinal) ablation dimension while also providing imaging (from an image-only or a treat-and image third transducer or from treat-and-image first and second transducers). In one example of the fifth embodiment, the first RF medical-treatment electrode is less expensive, and easier to taper to a tissue-penetrating edge, than using an ultrasound medical-treatment transducer in its place.

The present invention has, without limitation, application in conventional endoscopic, laparoscopic, and open surgical instrumentation as well as application in robotic-assisted surgery.

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention. It is understood that the embodiments of FIGS. 1-9 can include one or more additional ultrasound transducers than those shown, and that the embodiment of FIG. 10 can include one or more additional ultrasound transducers and/or one or more additional RF electrodes than those shown.

It is understood that any one or more of the following-described embodiments, examples, etc. can be combined with any one or more of the other following-described embodiments, examples, etc.

Figure 1:
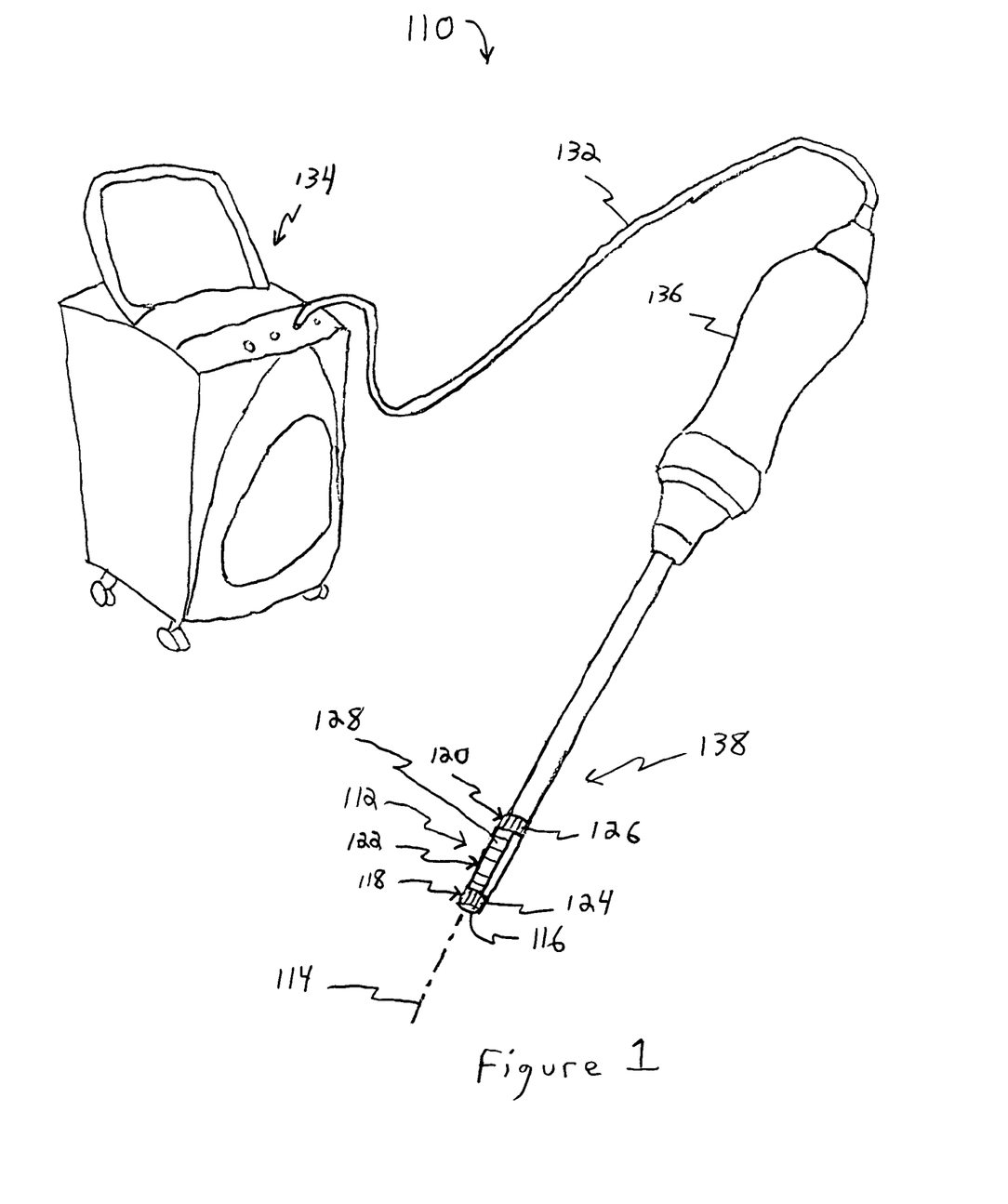
FIG. 1 is a schematic view of a first embodiment of an ultrasound medical treatment system of the invention.
Figures 2, 3:
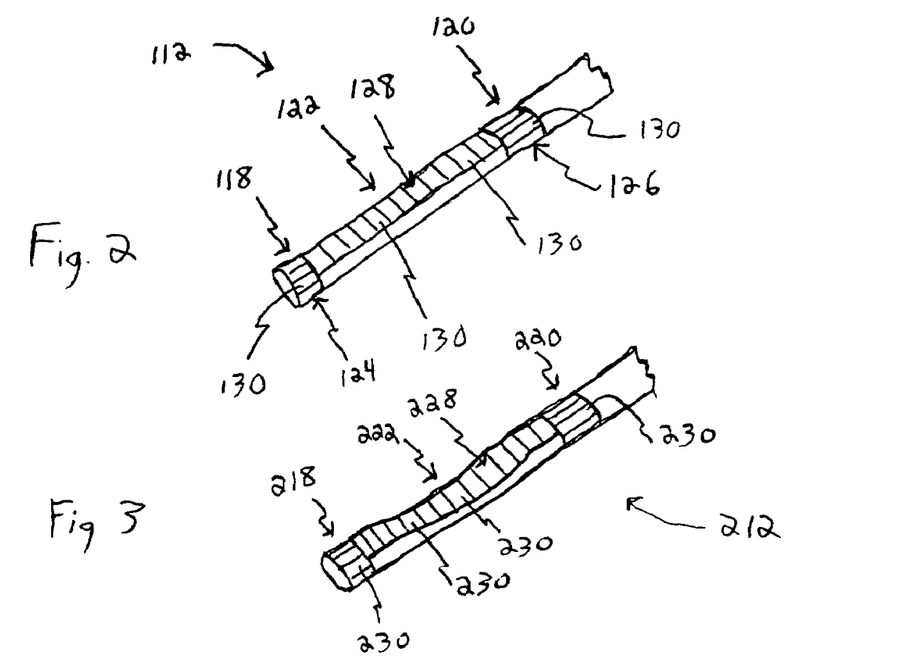
FIG. 2 is an enlarged view of the ultrasound transducer assembly of FIG. 1, wherein the ultrasound-emitting surface of the third ultrasound transducer is substantially-entirely planar.
FIG. 3 is a view, as in FIG. 2, but of an alternate embodiment of the ultrasound transducer assembly having a third ultrasound transducer whose ultrasound-emitting surface has a concave surface portion.

Referring now to the drawings, FIGS. 1-2 illustrate an embodiment of the present invention which is an ultrasound medical system 110 including an ultrasound transducer assembly 112. The ultrasound transducer assembly 112 has a longitudinal axis 114 and a distal end 116. The ultrasound transducer assembly 112 includes first, second and third ultrasound transducers 118, 120 and 122. It is noted that the phrase "ultrasound transducer" means ultrasound medical transducer. The first ultrasound transducer 118 is disposed proximate the distal end 116 and has a substantially-fully-cylindrical ultrasound-emitting surface 124 which is substantially coaxially aligned with, and outwardly-facing from, the longitudinal axis 114. The second ultrasound transducer 120 has a substantially-fully-cylindrical ultrasound-emitting surface 126 which is substantially coaxially aligned with, and outwardly-facing from, the longitudinal axis 114. The third ultrasound transducer 122 is disposed longitudinally between the first and second ultrasound transducers 118 and 120 and has an ultrasound-emitting surface 128 which is substantially-entirely planar or includes at least a concave surface portion.

In one arrangement of the embodiment of FIGS. 1-2, the first ultrasound transducer 118 is disposed at the distal end 116, and the third ultrasound transducer 122 is disposed proximate the first and second ultrasound transducers 118 and 120. In one variation, the third ultrasound transducer 122 abuts the first and second ultrasound transducers 118 and 120.

In one example of the embodiment of FIGS. 1-2, the ultrasound-emitting surface 128 of the third ultrasound transducer 122 is substantially-entirely planar. In an alternate embodiment of the ultrasound transducer assembly 212, shown in FIG. 3, the ultrasound-emitting surface 228 of the third ultrasound transducer 222 includes at least a concave surface portion. In one variation, the ultrasound-emitting surface of the third ultrasound transducer in its entirety has a substantially-cylindrically-focused shape (e.g., the ultrasound is focused substantially along a focal line, having a line thickness, such as a focal line which is parallel to, or perpendicular to, the longitudinal axis of the ultrasound transducer assembly). In another variation, the ultrasound-emitting surface of the third ultrasound transducer in its entirety has a substantially-spherically-focused shape (e.g., the ultrasound is focused substantially at a focal zone such as a dot having a dot size).

In one enablement of the embodiment of FIGS. 1-2, and/or the alternate embodiment of FIG. 3, the first and second ultrasound transducers 118 and 120 & 218 and 220 are ultrasound-medical-treatment-only ultrasound transducers. In the same or a different enablement, the third ultrasound transducer 122 and 222 is an ultrasound-medical-treatment-and-imaging ultrasound transducer. In one implementation of the embodiment of FIGS. 1-2, and/or the alternate embodiment of FIG. 3, at least one (and in one variation all) of the first, second and third ultrasound transducers 118-122 & 218-222 has a plurality of ultrasound transducer elements 130 & 230. In one variation, the transducer elements of an array of a plurality of transducer elements of an ultrasound transducer are electronically controlled together to steer and focus the ultrasound emitted by the array. It is noted that planar ultrasound transducer elements, when tilted inward, can be arranged to form an ultrasound transducer whose ultrasound-emitting surface has at least a concave portion. Similarly, planar ultrasound transducer elements, when not tilted, can be arranged to form an ultrasound transducer whose ultrasound-emitting surface is substantially-entirely planar. Likewise, planar ultrasound transducer elements, when tilted outward, can be arranged to form an ultrasound transducer having a substantially-fully-cylindrical ultrasound-emitting surface. In a different implementation, at least one (and in one variation all) of the first, second and third ultrasound transducers has only one ultrasound transducer element.

In one construction of the embodiment of FIGS. 1-2, a cable 132 operatively connects a controller 134 to the ultrasound transducer assembly 112. In one variation, the cable 132 connects the controller 134 to a handpiece 136 which is operatively connected to an end effector 138 which supports the ultrasound transducer assembly 112. In one modification, the end effector 138 is an articulated end effector 138, which is also rotatable about the longitudinal axis 114, allowing the user and/or the controller 134 to rotate and/or translate the ultrasound transducer assembly 112 as desired. In one procedure, the first and second ultrasound transducers 118 and 120 are used to ablate (which is one form of ultrasound medical treatment) patient tissue in contact with the end effector 138, along the end effector insertion track, which sterilizes such patient tissue and is useful, for example, when the end effector 138 passes through cancerous tissue which is to be medically treated with ultrasound from the ultrasound transducer assembly 112.

A broadened expression of the embodiments of FIGS. 1-3 is for an ultrasound medical system 110 comprising an ultrasound transducer assembly 112 and 212 having a longitudinal axis 114, having a distal end 116, and having two ultrasound transducers (122/222 and either 118/218 or 120/220). One of the ultrasound transducers (either 118/218 or 120/220) has a substantially-fully-cylindrical ultrasound-emitting surface (124 or 126) which is substantially coaxially aligned with, and outwardly-facing from, the longitudinal axis 114. Another of the ultrasound transducers 122/222 is disposed longitudinally proximal or distal to the one ultrasound transducer (either 118/218 or 120/220) and has an ultrasound-emitting surface 128 which is substantially-entirely planar or includes at least a concave surface portion.

In one example of the broadened expression of the embodiment of FIGS. 1-3, the one ultrasound transducer 118/218 is disposed proximate the distal end 116, and the other ultrasound transducer 122/222 is disposed proximate, and proximal to, the one ultrasound transducer 118/218.

Figure 4:
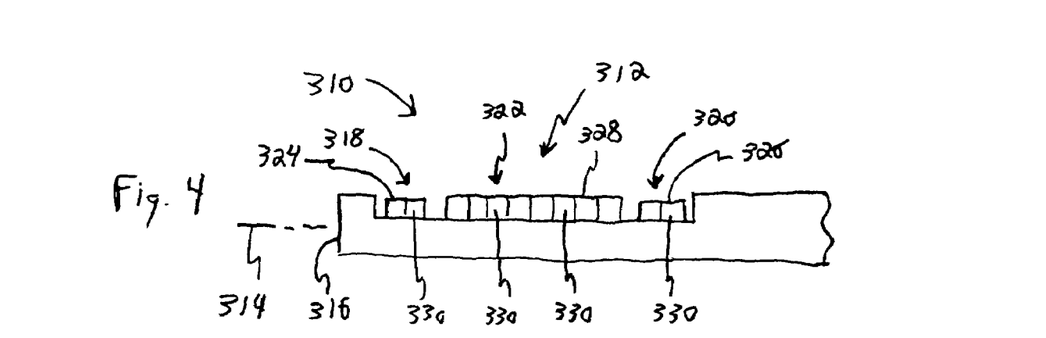
FIGS. 4-9 are side-elevational views of an ultrasound transducer assembly portion of additional embodiments of an ultrasound medical system of the invention, wherein the transducer assembly has three transducers whose ultrasound-emitting surfaces each are substantially-entirely planar or include at least a concave surface portion, and wherein the three transducers are various combinations of two types of treat-only, image-only and treat-and-image type ultrasound transducers.

Another embodiment of the invention is an ultrasound medical system 310 (only an ultrasound-transducer-assembly portion of which is shown in FIG. 4). The ultrasound medical system 310 includes an ultrasound transducer assembly 312 having a longitudinal axis 314. The ultrasound transducer assembly 312 includes first, second and third ultrasound transducers 318, 320 and 322 each having an ultrasound-emitting surface 324, 326 and 328 which is substantially-entirely planar or includes at least a concave surface portion. The first and second ultrasound transducers 318 and 320 are ultrasound-medical-treatment-only ultrasound transducers. The third ultrasound transducer 322 is an ultrasound-medical-treatment-and-imaging ultrasound transducer disposed longitudinally between the first and second ultrasound transducers 318 and 320.

In one arrangement of the embodiment of FIG. 4, the ultrasound transducer assembly 312 has a distal end 316. The first ultrasound transducer 318 is disposed proximate the distal end 316, and the third ultrasound transducer 322 is disposed proximate the first and second ultrasound transducers 318 and 320. In one variation, not shown, the third ultrasound transducer 322 abuts the first and second ultrasound transducers 318 and 320.

In one example of the embodiment of FIG. 4, the ultrasound-emitting surfaces 324, 326 and 328 of the first, second and third ultrasound transducers 318, 320 and 322 together are substantially-entirely planar. In an alternate embodiment of the ultrasound transducer assembly 412, shown in FIG. 5, at least one of the ultrasound-emitting surfaces 424, 426 and 428 of the first, second and third ultrasound transducers 418, 420 and 422 includes at least a concave surface portion. In one variation, the ultrasound-emitting surfaces of the first, second and third ultrasound transducers together in their entirety have a substantially-cylindrically-focused shape. In a different variation, the ultrasound-emitting surfaces of the first, second and third ultrasound transducers together in their entirety have a substantially-spherically-focused shape.

Figure 5:
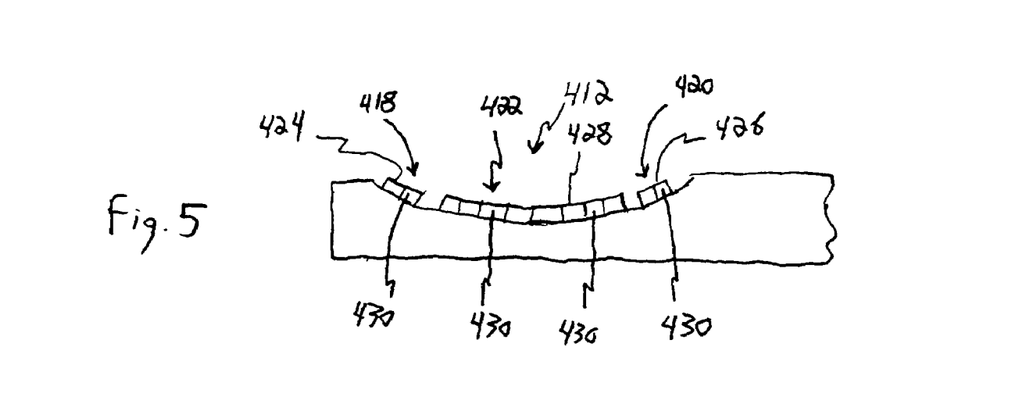

In one implementation of the embodiment of FIG. 4, and/or the alternate embodiment of FIG. 5, at least one (and in one variation all) of the first, second and third ultrasound transducers 318-322 & 418-422 has a plurality of ultrasound transducer elements 330 & 430. In a different implementation, at least one (and in one variation all) of the first, second and third ultrasound transducers has only one ultrasound transducer element.

Figure 6:
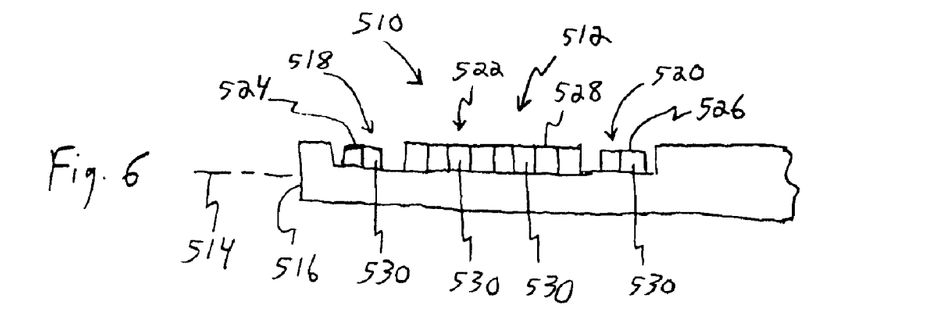

An additional embodiment of the invention is an ultrasound medical system 510 (only an ultrasound-transducer-assembly portion of which is shown in FIG. 6). The ultrasound medical system 510 includes an ultrasound transducer assembly 512 having a longitudinal axis 514. The ultrasound transducer assembly 512 includes first, second and third ultrasound transducers 518, 520 and 522 each having an ultrasound-emitting surface 524, 526 and 528 which is substantially-entirely planar or includes at least a concave surface portion. The first and second ultrasound transducers 518 and 520 are ultrasound-medical-treatment-only ultrasound transducers. The third ultrasound transducer 522 is an ultrasound-medical-imaging-only ultrasound transducer disposed longitudinally between the first and second ultrasound transducers 518 and 520.

In one arrangement of the embodiment of FIG. 6, the ultrasound transducer assembly 512 has a distal end 516. The first ultrasound transducer 518 is disposed proximate the distal end 516, and the third ultrasound transducer 522 is disposed proximate the first and second ultrasound transducers 518 and 520. In one variation, not shown, the third ultrasound transducer 522 abuts the first and second ultrasound transducers 518 and 520.

In one example of the embodiment of FIG. 6, the ultrasound-emitting surfaces 524, 526 and 528 of the first, second and third ultrasound transducers 518, 520 and 522 together are substantially-entirely planar. In an alternate embodiment, shown in FIG. 7, at least one of the ultrasound-emitting surfaces 624, 626 and 628 of the first, second and third ultrasound transducers 618, 620 and 622 includes at least a concave surface portion. In one variation, the ultrasound-emitting surfaces of the first, second and third ultrasound transducers together in their entirety have a substantially-cylindrically-focused shape. In a different variation, the ultrasound-emitting surfaces of the first, second and third ultrasound transducers together in their entirety have a substantially-spherically-focused shape.

Figure 7:
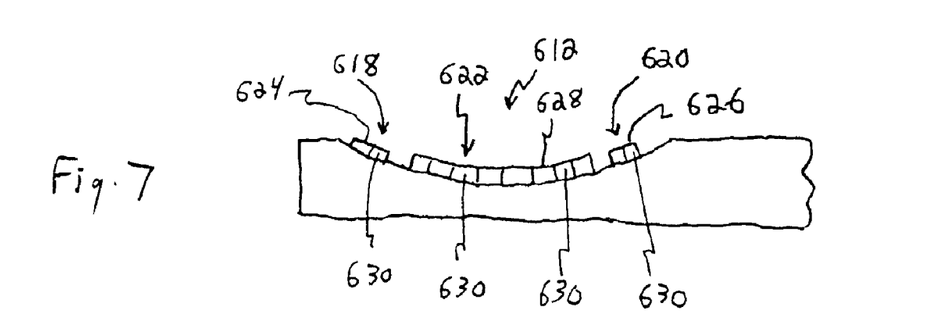

In one implementation of the embodiment of FIG. 6, and/or the alternate embodiment of FIG. 7, at least one (and in one variation all) of the first, second and third ultrasound transducers 518-522 & 618-622 has a plurality of ultrasound transducer elements 530 & 630. In a different implementation, at least one (and in one variation all) of the first, second and third ultrasound transducers has only one ultrasound transducer element.

Figure 8:
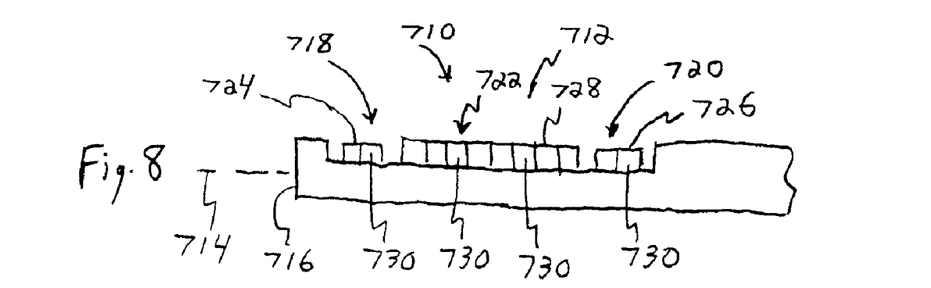

A further embodiment of the invention is an ultrasound medical system 710 (only an ultrasound-transducer-assembly portion of which is shown in FIG. 8). The ultrasound medical system 710 includes an ultrasound transducer assembly 712 having a longitudinal axis 714. The ultrasound transducer assembly 712 includes first, second and third ultrasound transducers 718, 720 and 722 each having an ultrasound-emitting surface 724, 726 and 728 which is substantially-entirely planar or includes at least a concave surface portion. The first and second ultrasound transducers 718 and 720 are ultrasound-medical-treatment-and-imaging ultrasound transducers. The third ultrasound transducer 722 is an ultrasound-medical-treatment-only ultrasound transducer disposed longitudinally between the first and second ultrasound transducers 718 and 720.

In one arrangement of the embodiment of FIG. 8, the ultrasound transducer assembly 712 has a distal end 716. The first ultrasound transducer 718 is proximate the distal end 716, and the third ultrasound transducer 722 is disposed proximate the first and second ultrasound transducers 718 and 720. In one variation, not shown, the third ultrasound transducer 722 abuts the first and second ultrasound transducers 718 and 720.

In one example of the embodiment of FIG. 8, the ultrasound-emitting surfaces 724, 726 and 728 of the first, second and third ultrasound transducers 718, 720 and 722 together are substantially-entirely planar. In an alternate embodiment, shown in FIG. 9, at least one of the ultrasound-emitting surfaces 824, 826 and 828 of the first, second and third ultrasound transducers 818, 820 and 822 includes at least a concave surface portion. In one variation, the ultrasound-emitting surfaces of the first, second and third ultrasound transducers together in their entirety have a substantially-cylindrically-focused shape. In a different variation, the ultrasound-emitting surfaces of the first, second and third ultrasound transducers together in their entirety have a substantially-spherically-focused shape.

Figure 9:
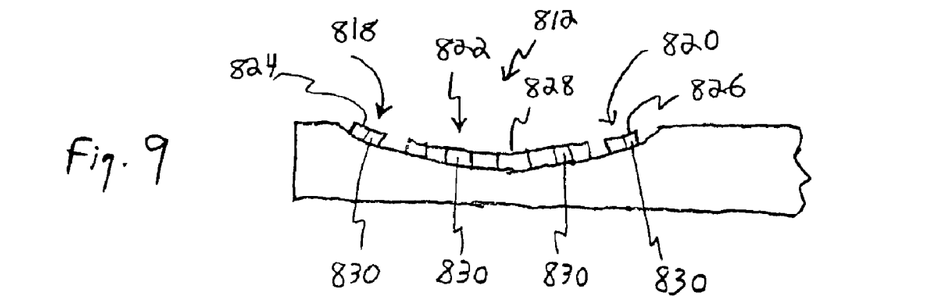

In one implementation of the embodiment of FIG. 8, and/or the alternate embodiment of FIG. 9, at least one (and in one variation all) of the first, second and third ultrasound transducers 718-722 & 818-822 has a plurality of ultrasound transducer elements 730 & 830. In a different implementation, at least one (and in one variation all) of the first, second and third ultrasound transducers has only one ultrasound transducer element.

A broadened expression of the embodiments of FIGS. 4-9 (with only part numbers from FIG. 4 being hereinafter listed for clarity) is for an ultrasound medical system 310 comprising an ultrasound transducer assembly 312 having a longitudinal axis 314, and having two ultrasound transducers (322 and either 318 or 320) each having an ultrasound-emitting surface (328 and either 324 or 326) which is substantially-entirely planar or includes at least a concave surface portion. One of the ultrasound transducers is disposed longitudinally proximal or distal to an other of the ultrasound transducers. The one and the other ultrasound transducers are different types of medical-treatment-only type, medical-treatment-and-imaging type, and medical-imaging-only type transducers. In one example, the one ultrasound transducer is a medical-treatment-only type ultrasound transducer and the other ultrasound transducer is a medical-treatment-and-imaging type ultrasound transducer. Other examples are left to the artisan. In one extension, the system 310 includes additional ultrasound transducers.

Figure 10:
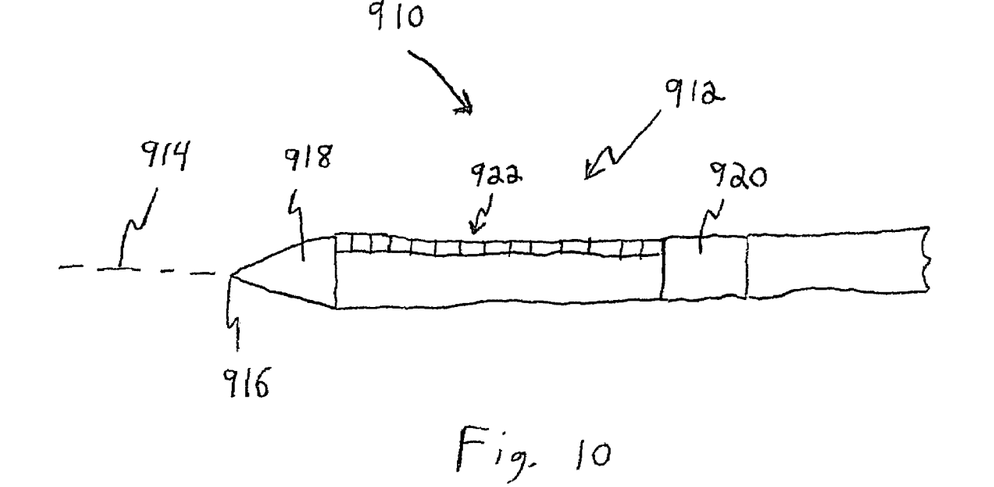
FIG. 10 is a side-elevational view of a transducer assembly portion of another embodiment of the ultrasound medical system of the invention.

Yet another embodiment of the invention is an ultrasound medical system 910 (only a transducer-assembly portion of which is shown in FIG. 10). The ultrasound medical system 910 includes a transducer assembly 912 having a longitudinal axis 914, having a distal end 916, having a first RF (radio-frequency) medical-treatment electrode 918, and having an ultrasound medical transducer 922 disposed longitudinally proximal or distal to the first RF medical-treatment electrode 918.

In one example of the embodiment of FIG. 10, the first RF medical-treatment electrode 918 is disposed proximate the distal end 916, and the ultrasound medical transducer 922 is disposed proximate, and longitudinally proximal to, the first RF medical-treatment electrode 918. In the same or a different example, the ultrasound medical system 910 also includes a second RF (radio-frequency) medical-treatment electrode 920, wherein the ultrasound medical transducer 922 is disposed longitudinally between the first and second RF medical-treatment electrodes 918 and 920. In the same or a different example, the first RF medical-treatment electrode 918 is disposed at the distal end 916 and tapers to a tissue-penetrating edge.

In one enablement of the embodiment of FIG. 10, the first and second RF medical-treatment electrodes 918 and 920 are bipoles of an RF system. In another enablement, the first and, when present, the second RF medical-treatment electrodes are monopoles of an RF system which also includes a dispersive electrode, not shown, as can be appreciated by those skilled in the art. In one variation, the RF system is phased between monopolar and bipolar. In one construction, the first and, when present, the second RF electrodes each are metallic rings (such as stainless steel or a copper alloy with gold plating), or are gold-plated plastic parts or gold-plated ceramic parts, or employ gold-plated flex circuit technology.

In one implementation of the embodiment of FIG. 10, the ultrasound medical transducer 922 is an ultrasound-medical-imaging-only ultrasound transducer. In a different implementation, the ultrasound medical transducer 922 is an ultrasound-medical-treatment-and-imaging ultrasound transducer. In another implementation, the ultrasound medical transducer 922 is an ultrasound-medical-treatment-only ultrasound transducer.

Several benefits and advantages are obtained from one or more of the embodiments of the ultrasound medical system of the invention. In one example of the embodiments of FIGS. 1-3, the first and second ultrasound transducers are ultrasound-medical-treatment-only ultrasound transducers and the third ultrasound transducer is an ultrasound-medical-treatment-and imaging ultrasound transducer which provides 360-degree treatment of patient tissue from the first and second transducers while also providing imaging (and treatment) from the third transducer. The embodiments of FIGS. 4-9) provide, in one example, treatment (from treat-only or treat-and-image first and second transducers) at the longitudinal ends of the transducer assembly which enhances the axial (longitudinal) ablation dimension while also providing imaging (from an image-only or a treat-and image third transducer or from treat-and-image first and second transducers). In one example of the embodiment of FIG. 10, the first RF medical-treatment electrode is less expensive, and easier to taper to a tissue-penetrating edge, than using an ultrasound medical-treatment transducer in its place.

Also, as can be appreciated by those skilled in the art, examples of one or more of the embodiments of the ultrasound medical system of the invention provide: better end-effector performance by optimally dividing the drive power over, for example, transducer piezo-electric material; means to more effectively increase the length of the transducer face to achieve tissue effects under high power (e.g., 10-120 watts per square centimeter) source conditions; means to achieve an adequate amount of tissue effect (ablation) at the ends of the transducer assembly (where the power output characteristically tends to be lower); means to achieve circumferential tissue ablation at the ends of the equatorial line of the created lesion (to minimize bleeding due to intervention, etc.); means to provide better mechanical strength to the end effector design (such as larger element size at the ends of the transducer assembly, cylindrical transducer end caps, etc.); and means to provide simpler device designs (such as a smaller number of elements, simpler packaging issues, fewer connecting cables, lower cost, etc.), yet maintain the treatment and imaging capability of the end effector.

While the present invention has been illustrated by a description of several embodiments, it is not the intention of the applicants to restrict or limit the spirit and scope of the appended claims to such detail. Numerous other variations, changes, and substitutions will occur to those skilled in the art without departing from the scope of the invention. For instance, the ultrasound medical system of the invention has application in robotic assisted surgery taking into account the obvious modifications of such systems and components to be compatible with such a robotic system. It will be understood that the foregoing description is provided by way of example, and that other modifications may occur to those skilled in the art without departing from the scope and spirit of the appended claims.

What is claimed is:

1. An ultrasound medical system comprising an ultrasound transducer assembly having a longitudinal axis, having a distal end, and having:
   a) a first ultrasound transducer disposed proximate the distal end and having a substantially-fully-cylindrical ultrasound-emitting outer exposed surface which is substantially coaxially aligned with, and outwardly-facing from, the longitudinal axis, wherein the first ultrasound transducer is an ultrasound-medical-treatment-only ultrasound transducer;
   b) a second ultrasound transducer having a substantially-fully-cylindrical ultrasound-emitting outer exposed surface which is substantially coaxially aligned with, and outwardly-facing from, the longitudinal axis, wherein the second ultrasound transducer is an ultrasound-medical-treatment-only ultrasound transducer; and
   c) a third ultrasound transducer disposed longitudinally between the first and second ultrasound transducers and having a plurality of planar transducer elements arranged to provide the third ultrasound transducer with an ultrasound-emitting outer exposed surface which is substantially-entirely planar or includes at least a concave surface portion.

2. The ultrasound medical system of claim 1, wherein the first ultrasound transducer is disposed at the distal end, and wherein the third ultrasound transducer is disposed proximate the first and second ultrasound transducers.

3. The ultrasound medical system of claim 1, wherein the ultrasound-emitting outer exposed surface of the third ultrasound transducer is substantially-entirely planar.

4. The ultrasound medical system of claim 1, wherein the ultrasound-emitting outer exposed surface of the third ultrasound transducer in its entirety has a substantially-cylindrically-focused shape.

5. The ultrasound medical system of claim 1, wherein the ultrasound-emitting outer exposed surface of the third ultrasound transducer in its entirety has a substantially-spherically-focused shape.

6. The ultrasound medical system of claim 1, wherein the third ultrasound transducer is an ultrasound-medical-treatment-and-imaging ultrasound transducer.

7. The ultrasound medical system of claim 1, wherein at least one of the first and second ultrasound transducers has only one ultrasound transducer element.

8. The ultrasound medical system of claim 1, wherein at least one of the first and second ultrasound transducers has a plurality of ultrasound transducer elements.

9. An ultrasound medical system comprising an ultrasound transducer assembly having a longitudinal axis, and having first, second and third ultrasound transducers each having a plurality of planar transducer elements arranged to provide each of the first, second, and third ultrasound transducers with an ultrasound-emitting outer exposed surface which includes at least a concave surface portion, wherein the first and second ultrasound transducers are ultrasound-medical-treatment-only ultrasound transducers, and wherein the third ultrasound transducer is an ultrasound-medical-treatment-and-imaging ultrasound transducer disposed longitudinally between the first and second ultrasound transducers.

10. The ultrasound medical system of claim 9, wherein the ultrasound transducer assembly has a distal end, wherein the first ultrasound transducer is disposed proximate the distal end, and wherein the third ultrasound transducer is disposed proximate the first and second ultrasound transducers.

11. The ultrasound medical system of claim 9, wherein the ultrasound-emitting outer exposed surfaces of the first, second and third ultrasound transducers together in their entirety have a substantially-cylindrically-focused shape.

12. The ultrasound medical system of claim 9, wherein the ultrasound-emitting outer exposed surfaces of the first, second and third ultrasound transducers together in their entirety have a substantially-spherically-focused shape.

13. An ultrasound medical system comprising an ultrasound transducer assembly having a longitudinal axis, and having first, second and third ultrasound transducers each having a plurality of planar transducer elements arranged to provide each of the first, second and third ultrasound transducers with an ultrasound-emitting outer exposed surface which includes at least a concave surface portion, wherein the first and second ultrasound transducers are ultrasound-medical-treatment-only ultrasound transducers, and wherein the third ultrasound transducer is an ultrasound-medical-imaging-only ultrasound transducer disposed longitudinally between the first and second ultrasound transducers.

14. The ultrasound medical system of claim 13, wherein the ultrasound transducer assembly has a distal end, wherein the first ultrasound transducer is disposed proximate the distal end, and wherein the third ultrasound transducer is disposed proximate the first and second ultrasound transducers.

15. The ultrasound medical system of claim 13, wherein the ultrasound-emitting outer exposed surfaces of the first, second and third ultrasound transducers together in their entirety have a substantially-cylindrically-focused shape.

16. The ultrasound medical system of claim 13, wherein the ultrasound-emitting outer exposed surfaces of the first, second and third ultrasound transducers together in their entirety have a substantially-spherically-focused shape.

17. An ultrasound medical system comprising an ultrasound transducer assembly having a longitudinal axis, and having first, second and third ultrasound transducers each having a plurality of planar transducer elements arranged to provide each of the first, second and third ultrasound transducers with an ultrasound-emitting outer exposed surface which includes at least a concave surface portion, wherein the first and second ultrasound transducers are ultrasound-medical-treatment-and-imaging ultrasound transducers, and wherein the third ultrasound transducer is an ultrasound-medical-treatment-only ultrasound transducer disposed longitudinally between the first and second ultrasound transducers.

18. The ultrasound medical system of claim 17, wherein the ultrasound transducer assembly has a distal end, wherein the first ultrasound transducer is disposed proximate the distal end, and wherein the third ultrasound transducer is disposed proximate the first and second ultrasound transducers.

19. The ultrasound medical system of claim 17, wherein the ultrasound-emitting outer exposed surfaces of the first, second and third ultrasound transducers together in their entirety have a substantially-cylindrically-focused shape.

20. The ultrasound medical system of claim 17, wherein the ultrasound-emitting outer exposed surfaces of the first, second and third ultrasound transducers together in their entirety have a substantially-spherically-focused shape.

21. An ultrasound medical system comprising an ultrasound transducer assembly having a longitudinal axis, having a distal end, and having two ultrasound transducers, wherein one of the ultrasound transducers has a substantially-fully-cylindrical ultrasound-emitting outer exposed surface which is substantially coaxially aligned with, and outwardly-facing from, the longitudinal axis, wherein an other of the ultrasound transducers is disposed longitudinally proximal or distal to the one ultrasound transducer and has a plurality of planar transducer elements arranged to provide the other ultrasound transducer with an ultrasound-emitting outer exposed surface which is substantially-entirely planar or includes at least a concave surface portion, and wherein the one ultrasound transducer is an ultrasound-medical-treatment-only ultrasound transducer.

22. The ultrasound medical system of claim 21, wherein the one ultrasound transducer is disposed proximate the distal end, and wherein the other ultrasound transducer is disposed proximate, and proximal to, the one ultrasound transducer.

\* \* \* \* \*